(12) United States Patent
Sato et al.

(10) Patent No.: US 8,030,784 B2
(45) Date of Patent: Oct. 4, 2011

(54) SEMICONDUCTOR NANOPARTICLE SURFACE MODIFICATION

(75) Inventors: Keiichi Sato, Tokyo (JP); Shinya Hattori, Tokyo (JP); Taeko Chiba, Tokyo (JP)

(73) Assignee: Hitachi Solutions, Ltd., Tokyo (JP)

( * ) Notice: Subject to any disclaimer, the term of this patent is extended or adjusted under 35 U.S.C. 154(b) by 814 days.

(21) Appl. No.: 11/606,895

(22) Filed: Dec. 1, 2006

(65) Prior Publication Data

US 2007/0131905 A1   Jun. 14, 2007

Related U.S. Application Data

(63) Continuation-in-part of application No. 11/325,533, filed on Jan. 5, 2006, now Pat. No. 7,329,369.

(30) Foreign Application Priority Data

Jan. 6, 2005  (JP) .................................. 2005-001583
Dec. 6, 2005  (JP) .................................. 2005-351558

(51) Int. Cl.
  *H01L 23/58* (2006.01)
  *C09K 11/02* (2006.01)
(52) U.S. Cl. ................... 257/798; 252/301.36; 977/773; 977/902
(58) Field of Classification Search .................. 257/798; 252/301.36; 977/773, 902
  See application file for complete search history.

(56) References Cited

U.S. PATENT DOCUMENTS

| | | | |
|---|---|---|---|
| 6,538,801 B2 * | 3/2003 | Jacobson et al. | 359/296 |
| 6,721,083 B2 * | 4/2004 | Jacobson et al. | 359/296 |
| 7,147,917 B2 * | 12/2006 | Adams et al. | 428/403 |
| 7,223,851 B2 * | 5/2007 | Terlesky et al. | 536/23.1 |
| 7,297,298 B2 * | 11/2007 | Matsunami et al. | 264/5 |
| 7,413,607 B2 * | 8/2008 | Rakow et al. | 117/68 |
| 7,491,286 B2 * | 2/2009 | Kagan et al. | 156/230 |
| 7,563,457 B2 * | 7/2009 | Cha et al. | 424/491 |
| 2002/0045045 A1 | 4/2002 | Adams et al. | |
| 2002/0150759 A1 * | 10/2002 | Jones et al. | 428/403 |
| 2003/0194731 A1 | 10/2003 | Sato et al. | |

(Continued)

FOREIGN PATENT DOCUMENTS

EP   1 333 280 A1   1/2003

(Continued)

OTHER PUBLICATIONS

Hao et al., Buildup of Polymer/Au Nanoparticle Multilayer Thin Films Based on Hydrogen Bonding, (2000), Chem. mater. 2000, 12, pp. 3392-3396.*

(Continued)

*Primary Examiner* — Evan Pert
*Assistant Examiner* — Teresa M Arroyo
(74) *Attorney, Agent, or Firm* — Stites & Harbison PLLC; Juan Carlos A. Marquez, Esq.

(57) ABSTRACT

Semiconductor nanoparticles having high luminescence properties that are preferable for applications and uses of biotechnology are provided.
With the use of electric charges on the surfaces of particles, the particles and selected polymers are allowed to electrostatically bind to each other, such that the surfaces of the particles are coated. The polymers are allowed to crosslink to each other, resulting in the improved durability of the particles. Further, functional groups contained in the polymers are exposed on the surfaces of the particles. Accordingly, semiconductor nanoparticles that are preferably utilized for applications such as staining and labeling of biopolymers have been synthesized.

16 Claims, 7 Drawing Sheets

U.S. PATENT DOCUMENTS

| | | | |
|---|---|---|---|
| 2005/0048570 A1* | 3/2005 | Weber et al. | 435/7.1 |
| 2005/0118731 A1* | 6/2005 | Salafsky | 436/518 |
| 2005/0170530 A1* | 8/2005 | Sato et al. | 438/1 |
| 2006/0068378 A1* | 3/2006 | Mirkin et al. | 435/5 |
| 2006/0081835 A1* | 4/2006 | Hutchison et al. | 257/17 |
| 2006/0088713 A1* | 4/2006 | Dykstra et al. | 428/402 |
| 2007/0065387 A1* | 3/2007 | Beck et al. | 424/70.13 |
| 2008/0202579 A1* | 8/2008 | Gur et al. | 136/252 |
| 2008/0241375 A1* | 10/2008 | Adams et al. | 427/221 |
| 2008/0293164 A1* | 11/2008 | Gaylord et al. | 436/536 |
| 2009/0017477 A1* | 1/2009 | Harma et al. | 435/7.72 |
| 2009/0221443 A1* | 9/2009 | Heller et al. | 506/16 |
| 2009/0325812 A1* | 12/2009 | Mirkin et al. | 506/8 |
| 2010/0086488 A1* | 4/2010 | Hoheisel et al. | 424/9.3 |

FOREIGN PATENT DOCUMENTS

| | | |
|---|---|---|
| EP | 1 514 909 A2 | 8/2004 |
| EP | 1 679 359 A1 | 12/2005 |
| WO | WO 02/055186 A2 | 10/2001 |

OTHER PUBLICATIONS

Bassani et al., Harnessing Supramolecular Interactions in Organic Solid-State Devices: Current Status and Future Potential, (2010), Coordination Chemistry Reviews 254, pp. 2429-2445.*

Nann, Semiconductor Nanoparticles: New Building Blocks for Polymer-Microelectronics?, (2001), Session 2: Polymer Electronic Devices I, pp. 49-53.*

Shipway et al., Nanoparticles as Structural and Functional Units in Surface-Confined Architectures, (2001), Chem. Commun., pp. 2035-2045.*

* cited by examiner

After coating

Before coating

SEMICONDUCTOR NANOPARTICLE SURFACE MODIFICATION

CROSS-REFERENCE TO RELATED APPLICATION

This application is a Continuation-in-Part application of U.S. application Ser. No. 11/325,533 filed Jan. 5, 2006 now U.S. Pat. No. 7,329,369. Priority is claimed based on U.S. application Ser. No. 11/325,533 filed Jan. 5, 2006, which claims the priority of Japanese Patent Application No. 2005-001583 filed on Jan. 6, 2005, all of which is incorporated by reference.

BACKGROUND OF THE INVENTION

1. Field of the Invention

The present invention relates to a semiconductor nanoparticle having high luminescence properties and a method for synthesizing the same. Moreover, the present invention relates to a fluorescent reagent and an optical device comprising such semiconductor nanoparticle.

2. Background Art

Semiconductor nanoparticles with particle sizes of 10 nm or less are located in the transition region between bulk semiconductor crystals and molecules, so that they exhibit physicochemical properties different from those of either bulk semiconductor crystals or molecules. In such region, the degeneracy of energy bands that is observed in bulk semiconductors is removed and the orbits become discrete, so that a quantum size effect appears in which the energy width of the forbidden band changes depending on particle size. According to the appearance of the quantum size effect, the energy width of the forbidden band of a semiconductor nanoparticle decreases or increases in response to an increase or decrease of particle size. This change of the energy width of the forbidden band affects the fluorescence properties of the particle in question. A particle that has a smaller particle size and wider forbidden band energy width tends to have a shorter a fluorescent wavelength, while a particle that has a larger particle size and a narrower forbidden band energy width tends to have a longer fluorescent wavelength. That is, it is possible to create a desired fluorescent color by controlling particle size. In addition to the properties described above, semiconductor nanoparticles have high durability against excitation lights, etc., and a region which can be excited widely extends more towards the shorter wavelengths than the fluorescent wavelength, so that simultaneous excitation of multiple fluorescent colors is also possible by using a single excitation light source. Thus, semiconductor nanoparticles serving as fluorescent material are gaining significant attention. Specifically, the fields related to biotechnology and to optical device technology are listed as fields in which semiconductor nanoparticles have been used actively, and further applications are expected in the future.

In order to use semiconductor nanoparticles serving as fluorescence material, it is desired that such particles have fluorescence properties in which the fluorescence spectrum has a waveform with a narrow and sharp full width half maximum (FWHM). Thus, it is necessary that the band gap fluorescence properties in response to the forbidden band widths of the semiconductor nanoparticles are made effective. However, even if a prepared bulk particle has a monodisperse particle size, such particle per se does not exhibit sufficient band gap fluorescence properties. As a reason for this, the presence of the energy level existing mainly at the surface site of the semiconductor nanoparticle is mentioned, and, since the energy level exists in the forbidden band inside the particle, it has been thought that the band gap fluorescence properties are inhibited. Due to the reasons mentioned above, the inactivation of the aforementioned energy level and the obtaining of the band gap fluorescence have become significant subjects.

A method for providing a solution to this subject relates to a (CdSe)ZnS semiconductor nanoparticle, which has a so-called core-shell type structure. The aforementioned method involves obtaining high luminescence properties by coating the semiconductor nanoparticle (CdSe) with a second semiconductor material (ZnS), which has a wider forbidden band width than that of the particle, and removing the energy level in the forbidden band of the particle, thereby making the band gap fluorescence properties effective. (JP Patent Publication (Kohyo) No. 2001-523758 A and J. Phys. Chem. B. 101:9463 (1997))

In addition, by achieving particle size monodispersion in an aqueous solution and carrying out particle surface reforming, inventors have been studying a method for making band gap fluorescence effective. As a result of intensive studies carried out by the inventors, a method for obtaining semiconductor particles having commercially adequate fluorescence properties has been developed, in which semiconductor nanoparticles synthesized by a size-selective photoetching technique are treated in a refining process, the particles are subjected to surface reforming using sodium hydroxide or amine-ammonium compounds, and the energy levels at the particle surfaces are made inactive by arranging the electron-releasing groups on the surfaces, such that the band gap fluorescence properties are made effective. Moreover, by coating the obtained nanoparticles with organic compounds such as one composed of amphiphilic molecules, we succeeded in obtaining semiconductor nanoparticles having improved chemical durability. According to a series of these methods, synthesis of semiconductor nanoparticles that have high luminescence properties was realized by using a safe and simple technique in an aqueous solution. The nanoparticles per se have sufficient durability. In addition, high durability can be imparted to them by allowing preferably usable organic compounds, such as amphipathic molecules, to bind to each other. However, for the purpose of synthesizing high-functional semiconductor nanoparticles by a more convenient method, the inventors have arrived at the present invention.

SUMMARY OF THE INVENTION

The inventors have invented a surface treatment, such as an OH coating or ammonia treatment, as a surface reforming technique for semiconductor nanoparticles. However, semiconductor nanoparticles that have been subjected to a surface treatment, such as an OH coating or ammonia treatment, do not have sufficient durability against external factors, typically including pH. It has been an objective to solve the aforementioned problems.

In order to protect semiconductor nanoparticles from the aforementioned external factors, the inventors have attempted a method of coating obtained nanoparticles with organic material. Further, the inventors have conducted studies of semiconductor nanoparticles having chemical durability and showing high luminescence properties. When semiconductor nanoparticles are utilized for bio-related applications, it is preferable to modify the surfaces of such semiconductor nanoparticles with a functional group such as a carboxyl group. Also, it is necessary to modify semiconductor nanoparticles so as to improve the industrial availability thereof.

The inventors found that semiconductor nanoparticles exerting high luminescence properties can be obtained by applying surface reforming to semiconductor nanoparticles, and modifying the semiconductor nanoparticles with a functional group-containing polymer, thereby allowing the polymer to form a crosslink via a crosslinking agent.

That is, firstly, the present invention is an invention of a semiconductor nanoparticle exerting high luminescence properties, which is modified with a functional group-containing polymer that electrostatically binds to the semiconductor nanoparticle.

Preferably, electron-releasing groups are arranged on the surface of the semiconductor nanoparticle, and the polymer electrostatically binds to the outside of the electron-releasing groups. Preferably, the functional group-containing polymer electrostatically binds to the surface of the semiconductor nanoparticle, and the modifying groups of the functional group-containing polymer form a crosslinking bond via a crosslinking agent.

Preferably, specific examples of functional groups of the functional group-containing polymer include, but are not limited to, one or more functional groups selected from the group consisting of —COOH, —OH, —NH$_2$, —SH, —OCN, —CNO, —CHO, —CH=O, —CH=CH$_2$, and —C≡CH, so that various types of crosslinking reactions can be involved.

The functional group-containing polymer may directly bind to the surface of a semiconductor nanoparticle or bind thereto via a semiconductor nanoparticle-coating compound.

Preferably, specific examples of the crosslinking bond include one or more bonds selected from the group consisting of an ester bond, an amide bond, an imide bond, an ether bond, a urethane bond, a sulfide bond, a polysulfide bond, a carbonate bond, a thiol bond, a thioester bond, and a thiourethane bond. The crosslinking bond comprises a crosslink that results from carbon-carbon double bond or carbon-carbon triple bond polymerization.

In preferred examples, the functional group-containing polymer is polyacrylic acid and the crosslinking agent is alkylene diamine.

Preferably, examples of the electron-releasing group include at least one group selected from the group consisting of —OR, —OCH$_2$R, —OCOCH$_2$R, —NHR, —N(CH$_2$R)$_2$, —NHCOCH$_2$R, —CH$_2$R, and —C$_6$H$_4$R, where R is hydrogen, a substituted hydrocarbon group, or an unsubstituted hydrogen group. In addition, preferably, examples of the semiconductor nanoparticle surface-coating compound include one or more compounds selected from the group consisting of primary amines (R$_1$NH$_2$), in particular alkyl amines having more than 7 carbons, more preferably C$_{8-24}$ alkyl amines, secondary amines (R$_1$R$_2$NH), tertiary amines (R$_1$R$_2$R$_3$N), and quaternary ammonium compounds (R$_4$R$_5$R$_6$R$_7$N$^+$), where R$_1$ to R$_7$ are each hydrogen, a substituted hydrocarbon group, or an unsubstituted hydrogen group and R$_1$ to R$_7$ preferably comprise a substituent at a terminal opposite to an amino group or ammonium group.

Preferably, specific examples of the semiconductor nanoparticle material include, but are not limited to, one or more materials selected from the group consisting of ZnO, ZnS, ZnSe, ZnTe, CdO, CdS, CdMnS, CdSe, CdMnSe, CdTe, CdMnTe, HgS, HgSe, HgTe, InP, InAs, InSb, InN, GaN, GaP, GaAs, GaSb, TiO$_2$, WO$_3$, PbS, PbSe, MgTe, AlAs, AlP, AlSb, AlS, Ge, and Si. In addition, a semiconductor nanoparticle having a multilayer structure consisting of a core portion and a shell portion may be made of one or more member of the aforementioned group.

The particle size of the semiconductor nanoparticle of the present invention exhibits a deviation of less than 10% rms in diameter, thereby achieving monodispersion.

Moreover, the semiconductor nanoparticle of the present invention is characterized in that it emits light in a narrow spectrum range of less than 60 nm in terms of full width at half maximum (FWHM) upon being irradiated with excitation light.

Secondly, the present invention is an invention of a method for manufacturing a semiconductor nanoparticle, which comprises a process for allowing a functional group-containing polymer to electrostatically bind to the surface of the semiconductor nanoparticle, a process for causing functional groups of the polymer to form a crosslink via a crosslinking agent.

Specifically, the method comprises a process for arranging electron-releasing groups on the surface of a semiconductor nanoparticle by adding surface-treating material having one or more electron-releasing groups to the semiconductor nanoparticle, a process for allowing a functional group-containing polymer to electrostatically bind to the arranged electron-releasing groups, and a process for causing functional groups of the functional group-containing polymer to form a crosslink via a crosslinking agent.

As above, preferably, examples of functional groups of the functional group-containing polymer include, but are not limited to, one or more groups selected from the group consisting of —COOH, —OH, —NH$_2$, —SH, —OCN, —CNO, —CHO —CH=O, —CH=CH$_2$, and —C≡CH.

Preferably, examples of the crosslinking reaction include one or more reactions selected from the group consisting of an esterification reaction, an amidation reaction, an imidation reaction, an etherification reaction, an urethanation reaction, a sulfidation reaction, a polysulfidation reaction, a carbonate reaction, a thiolation reaction, a thioesterification reaction, and a thiourethanation reaction. A carbon-carbon double bond or carbon-carbon triple bond polymerization reaction is also effective for the formation of an organic layer as an outer shell of the semiconductor nanoparticle.

Particularly, in preferred examples, the functional group-containing polymer is polyacrylic acid and the crosslinking agent is alkylene diamine. Specifically, a semiconductor nanoparticle having further improved durability and a surface condition that is particularly preferable for bio-related applications is obtained by allowing a polymer such as polyacrylic acid to electrostatically bind to the surface of a semiconductor nanoparticle that has been coated with organic compounds or by surface reforming with the use of electric charges on the surface of the semiconductor nanoparticle, and further by allowing the polymer to form a crosslinking bond with another polymer with the use of ethylenediamine, 1-ethyl-3-(3-dimethylaminopropyl)carbodiimide (EDC), or the like.

Preferably, examples of a surface-treating material that provides electron-releasing groups to a semiconductor nanoparticle surface include at least a pure metal, a metal compound, nitrogenated compounds selected from the group consisting of ammonia, amines, ammoniums, nitriles, and isocyanates, or oxygenated compounds selected from the group consisting of alcohols, phenols, ketones, aldehydes, carboxylic acids, esters of organic or inorganic acids, ethers, acid amides, and acid anhydrides.

Preferably, examples of the semiconductor nanoparticle-coating material include at least one material selected from the group consisting of primary amines (R$_1$NH$_2$), secondary amines ($R_1R_2NH$), tertiary amines ($R_1R_2R_3N$), and quaternary ammonium compounds ($R_4R_5R_6R_7N^+$), where $R_1$ to $R_7$ are each hydrogen, a substituted hydrocarbon group, or an unsubstituted hydrocarbon group, and $R_1$ to $R_7$ preferably comprise a substituent at a terminal opposite to an amino group or ammonium group.

Thirdly, the present invention is an invention regarding semiconductor nanoparticle applications, and the invention relates to a fluorescent reagent and an optical device.

According to the present invention, semiconductor nanoparticles that are available for use in industries related to bio-applications can be synthesized. Further, reagents that are relatively safer than those used in existing methods can be used, so that a synthesis method that is performed under safe reaction conditions can be selected. Thus, semiconductor nanoparticles that are suitable for mass synthesis and the like can be produced in a more industrially adequate manner.

DESCRIPTION OF THE PREFERRED EMBODIMENTS

Figure 1:
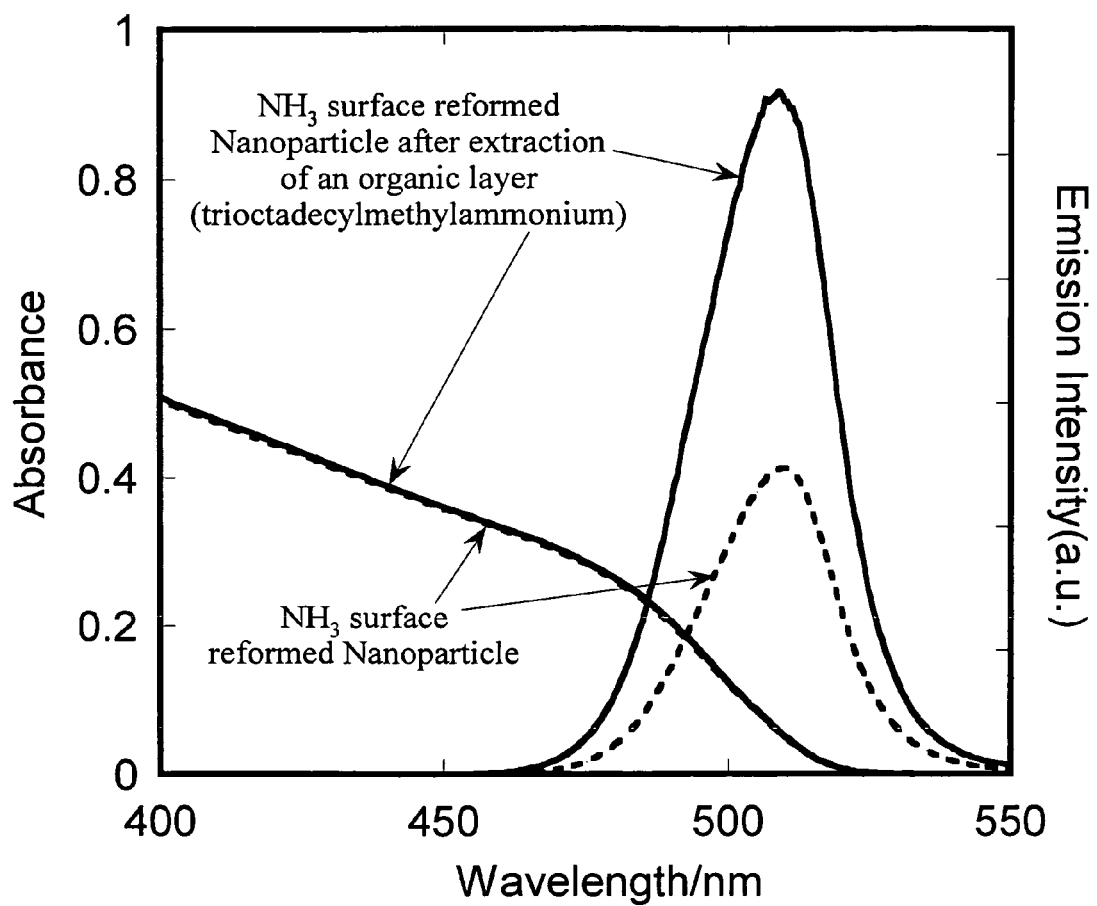
FIG. 1 shows absorbance and fluorescence spectra of a $NH_3$ surface reformed semiconductor nanoparticle and a semiconductor nanoparticle obtained by adding an ammonium compound to an aqueous solution containing the surface reformed semiconductor nanoparticle.

The preferred embodiments for carrying out the present invention will be described below.

EXAMPLES (In the Case of using a Size Selective Photoetching Technique)

First, 61.8 mg of sodium hexametaphosphate (0.1 mmol) and 84.4 mg of cadmium perchlorate (0.2 mmol) were added to a container filled with 1000 ml of 30° C. ultrapure water, 141.960 mg of disodium hydrogenphosphate (1 mmol) was added thereto, and then this solution was stirred for 30 minutes in a container that was sealed while nitrogen was bubbled thereinto. After that, 4.96 $cm^{-3}$ (1 atm, 25° C.) of hydrogen sulfide gas was added to the aforementioned container to result in equal amounts of $S^{2-}$ and $Cd^{2+}$ while the container was strongly shaken, and the solution was agitated for several hours at room temperature. At this time, the color of the solution changed from optically clear colorless to optically clear yellow. Moreover, after removing unreacted hydrogen sulfide in the solution by bubbling nitrogen into the solution, oxygen bubbling was carried out for 10 minutes and 25.7 mg of methyl viologen (0.1 mmol) was added to the solution. Here, the aforementioned solution was irradiated with monochromatic light using a laser, etc. or light from a mercury vapor lamp that had passed through a color filter to control the particle size using a size selective photoetching technique. Then, after the aforementioned solution was agitated for 30 minutes while nitrogen was bubbled into the solution, 50 μl of 3-mercaptopropionic acid was added thereto and the resultant was agitated for one night under shading.

(In the Case of not using a Size Selective Photoetching Technique)

First, 61.8 mg of sodium hexametaphosphate (0.1 mmol) and 84.4 mg of cadmium perchlorate (0.2 mmol) were added to a container filled with 1000 ml of 30° C. ultrapure water, 28.392 mg of disodium hydrogenphosphate (0.2 mmol) and 95.984 mg of sodium dihydrogenphosphate (0.8 mmol) were added thereto, and then this solution was stirred for 30 minutes in a container that was sealed up while nitrogen was bubbled thereinto. After that, 4.96 $cm^{-3}$ (1 atm, 25° C.) of hydrogen sulfide gas was added to the aforementioned container to result in equal amounts of $S^{2-}$ and $Cd^{2+}$ while the container was strongly shaken, and the solution was agitated for several hours at room temperature. Moreover, after removing unreacted hydrogen sulfide in the solution by bubbling nitrogen into the solution, 50 μl of 3-mercaptopropionic acid was added to the solution, followed by agitation for one night under shading.

1000 ml of solution prepared by either method described above was ultra-filtered and concentrated to several milliliters so as to remove methyl viologen, hexametaphosphoric acid, unreacted thiol compound, and ions, etc. dissolved upon photoetching from the aqueous solution, such that a solution containing semiconductor nanoparticles having surfaces modified with a pure thiol compound was prepared. Then, it was ultra-filtered by adding pure water and refined by repeating this process several times. Thereafter, a surface reforming treatment was performed by using the solution, which was finally concentrated to several milliliters.

The refined thiol-modified semiconductor nanoparticle solution obtained as described above was diluted by using 0.1 M $NH_3$ aq. so as to have an absorbance of 0.5, and surface treatment was carried out by allowing it stand for several days under irradiating fluorescent light. Accordingly, a semiconductor nanoparticle solution having high luminescence properties was obtained. The obtained solution was optically clear yellow and it had excellent luminescence properties. Fluorescence spectra from such time are shown in FIG. 1.

A mixed solution made by adding tridodecylmethylammonium chloride to an organic solvent such as hexane to a concentration of 1 mg/ml with respect to the solvent was added to the aforementioned surface reformed semiconductor nanoparticle solution in an amount such that it accounted for 1/10 of the amount of the solution. Or, alternatively, a mixed solution made by adding trioctadecylmethylammonium bromide to an organic solvent to a concentration of 2 mg/ml with respect to the solvent was added to the surface reformed semiconductor nanoparticle solution in an amount such that it accounted for 1/10 of the amount of the solution, and methanol was added thereto in an amount such that it accounted for 1/5 of the amount of the solution. Either one of these resulting solutions was strongly agitated for a certain time. As a result, it could be confirmed that the optically clear yellow part was transferred from the aqueous phase to the organic phase. Then, after performing a centrifugal separation, the aqueous phase and the organic phase were separated. The aforementioned recovered organic phase was diluted by adding an organic solvent such as hexane so as to result in the same absorbance as that of the aforementioned aqueous solution before transfer. The semiconductor nanoparticles transferred to the organic phase still maintained high luminescence properties. Fluorescence spectra from such time are shown in FIG. 1.

Example 1

Figure 2:
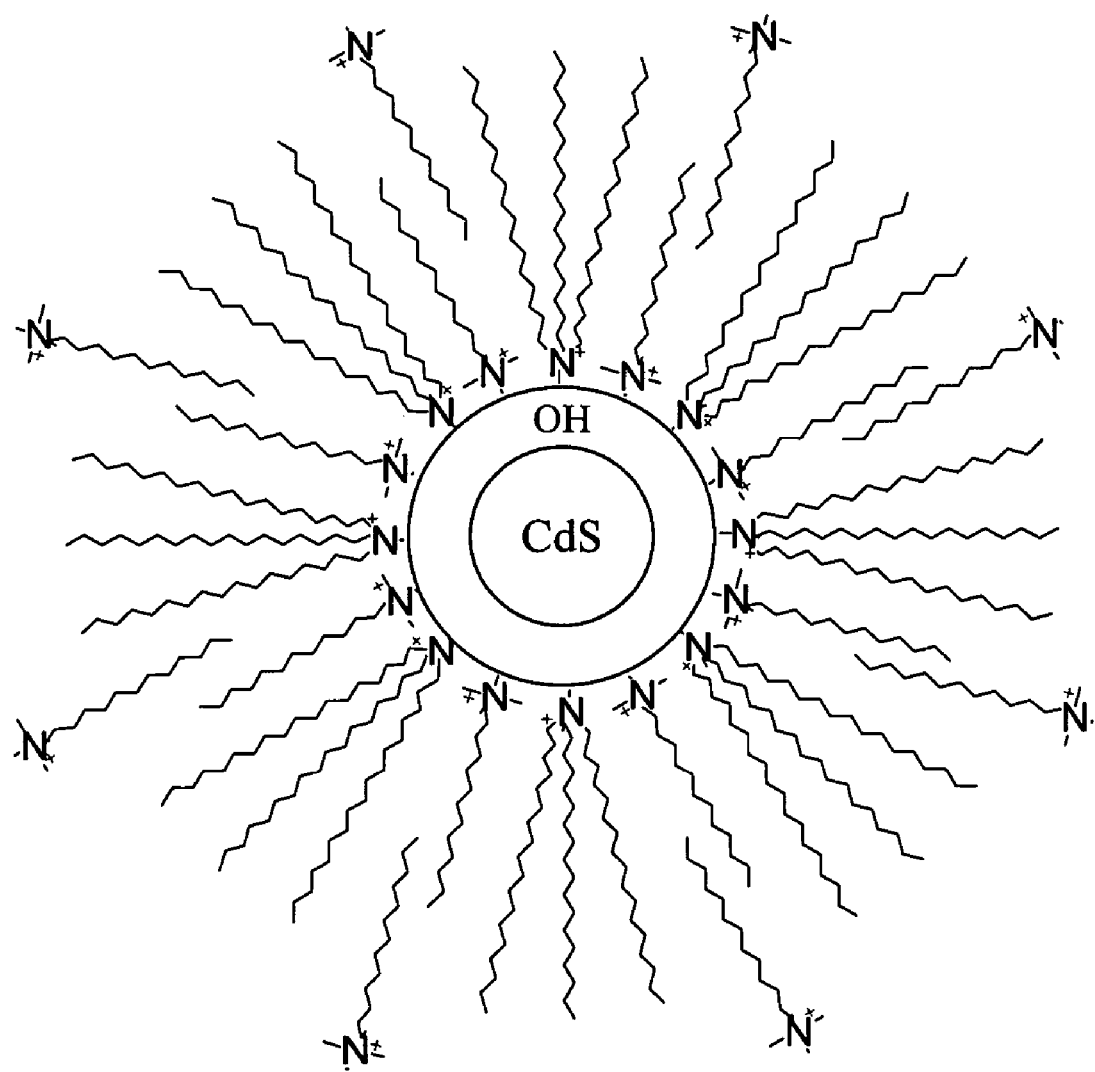
FIG. 2 shows a schematic diagram of a semiconductor nanoparticle obtained by adding an ammonium compound to a $NH_3$ surface reformed semiconductor nanoparticle.
Figure 3:
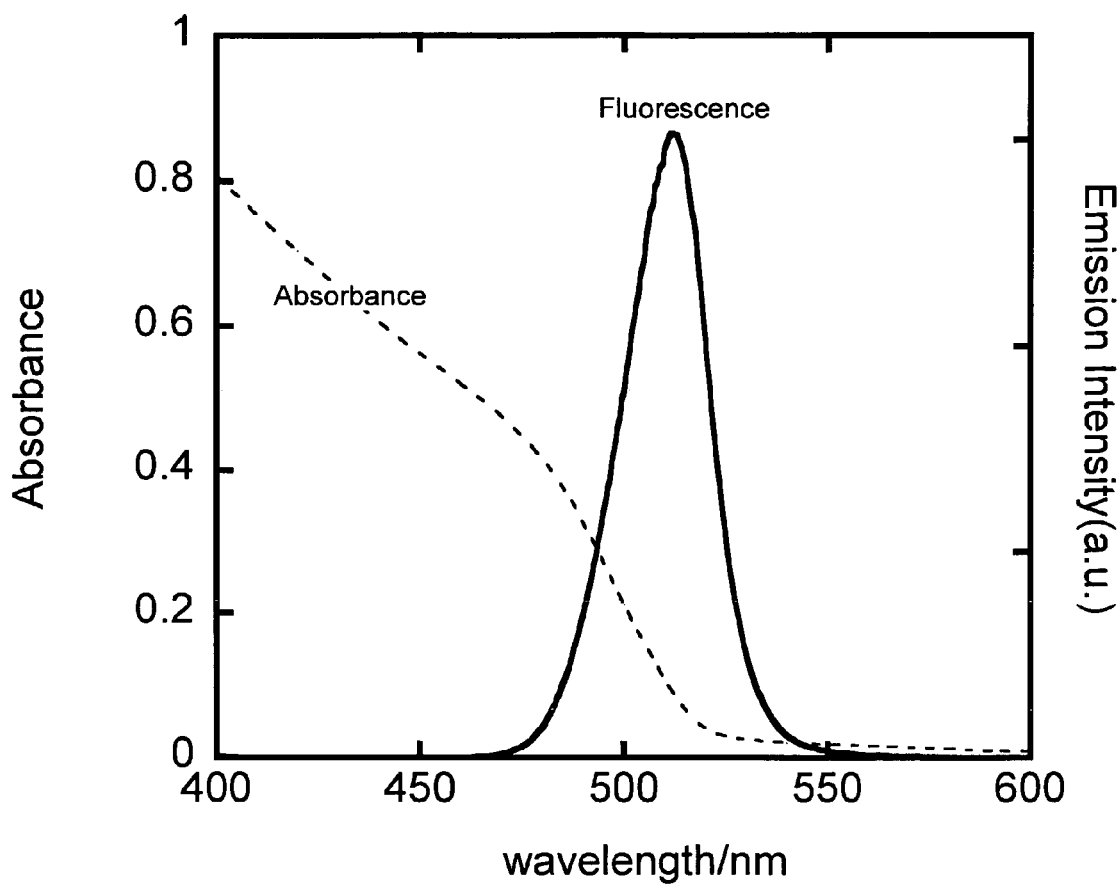
FIG. 3 shows absorbance and fluorescence spectra of a semiconductor nanoparticle obtained by adding an ammonium compound to a $NH_3$ surface reformed semiconductor nanoparticle.

Nanoparticles perfectly dispersed into the organic solvent obtained as mentioned above were coated with amphipathic molecules. 10 ml of a solution in which nanoparticles had perfectly dispersed into the aforementioned organic solvent was put into a container such as a stoppered test tube or an eggplant shaped flask, etc. and was made to assume a membranous form on the inner wall of the container by evaporation. Then, the particles were dissolved again by adding 2 ml of solution in which dodecyltrimethylammonium chloride was dissolved in chloroform to a concentration of 5 mM, and the resulting solution was made to assume a membranous form again on the inner wall of the container by evaporation. Moreover, after removing residual chloroform by heating the container at 90° C., the particles were dissolved again by adding 2 ml of methanol. Then, methanol was removed by adding 10 ml of ultrapure water, followed by agitation for some time during heating to 90° C. Finally, an optically clear yellow solution could be obtained by performing centrifugal separation so as to remove the precipitation. A schematic drawing and optical spectra at this time are shown in FIGS. 2 and 3, respectively.

Figure 4:
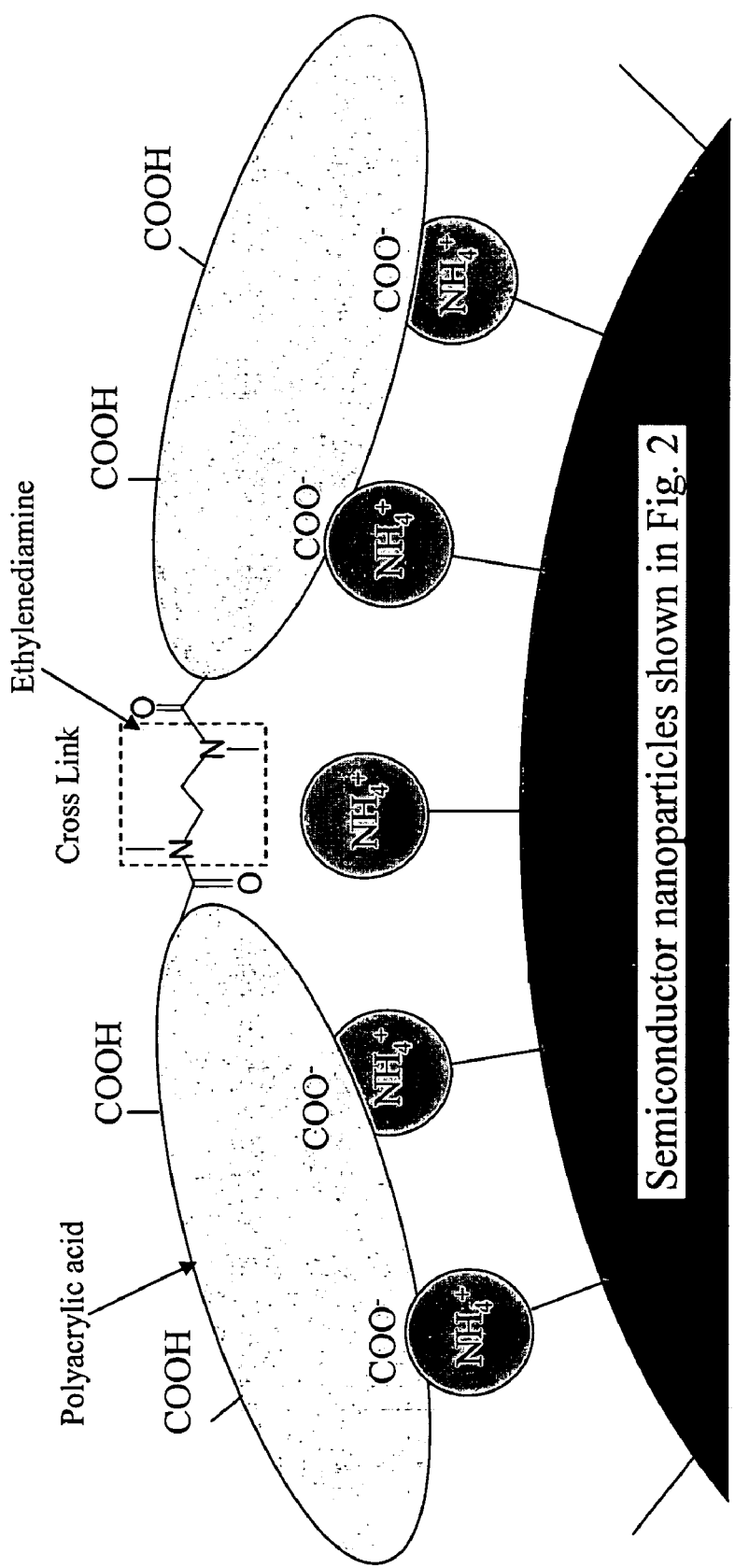
FIG. 4 shows a schematic drawing of semiconductor nanoparticles comprising a crosslink formed with polyacrylic acid and ethylenediamine.
Figure 5:
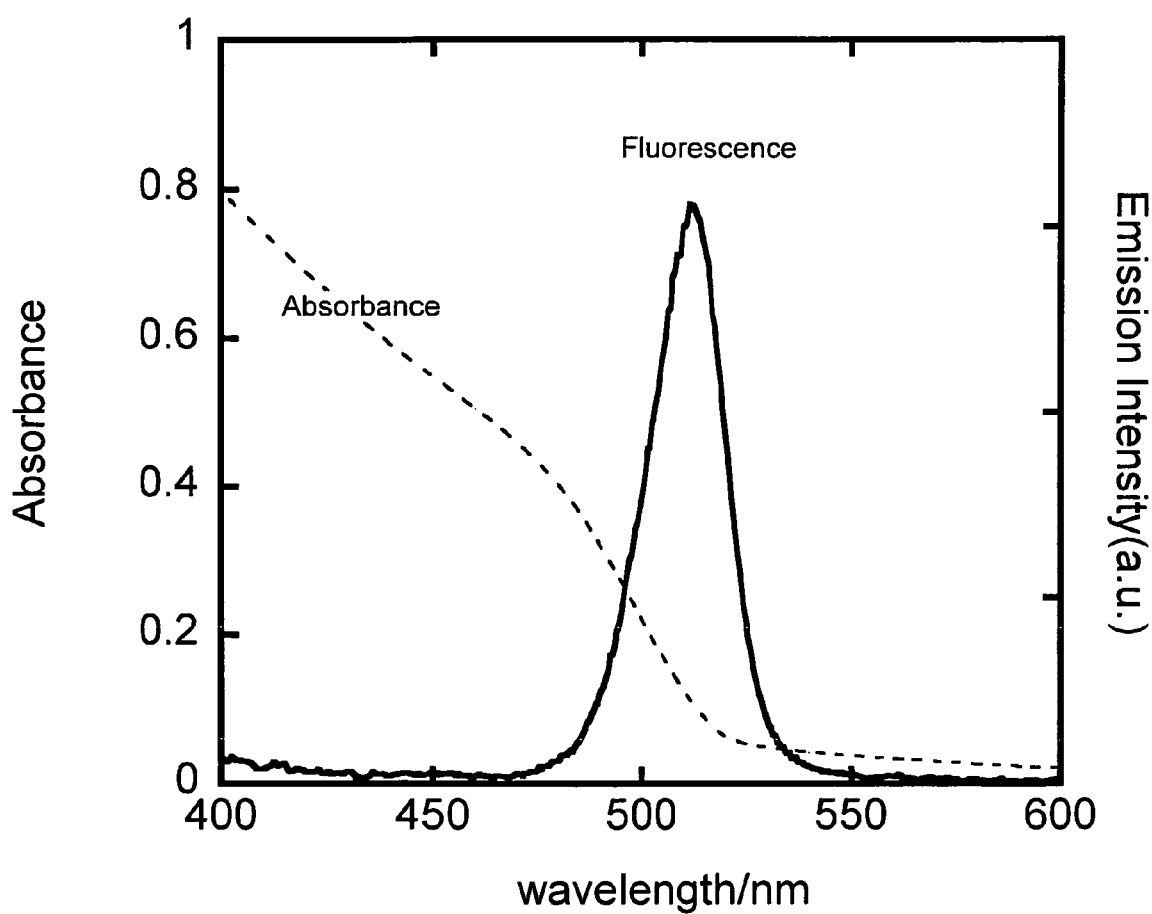
FIG. 5 shows absorbance and fluorescence spectra of a semiconductor nanoparticle comprising a crosslink formed with polyacrylic acid and ethylenediamine.
Figure 6:
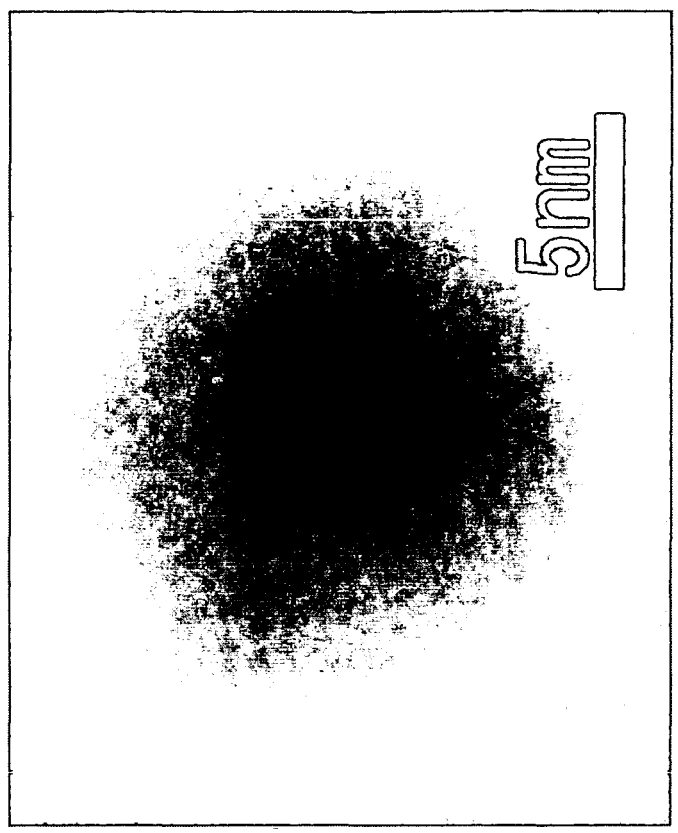
FIG. 6 shows transmission electron microscope (TEM) pictures of a semiconductor nanoparticle comprising a crosslink formed with polyacrylic acid and ethylenediamine.
Figure 6:
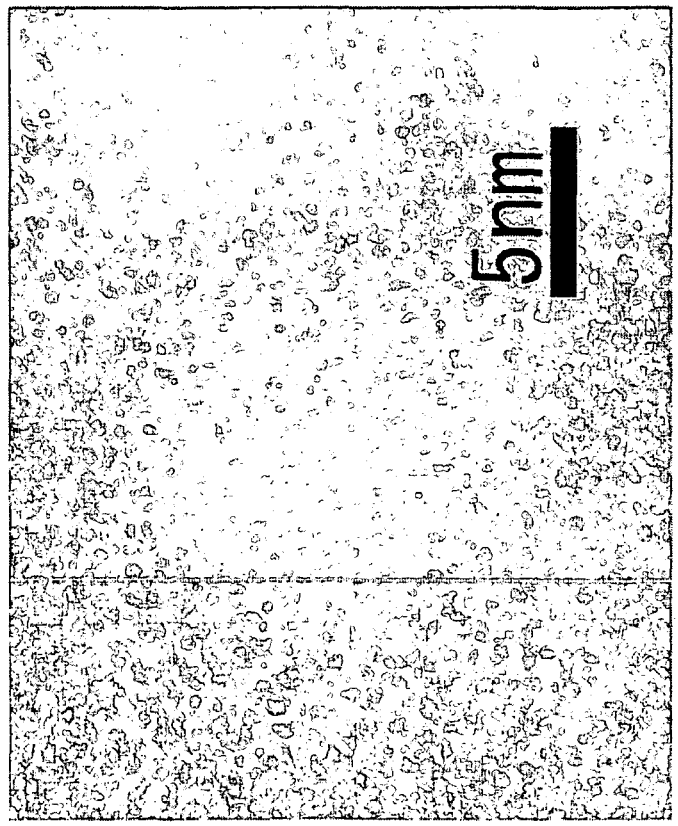
Figure 7:
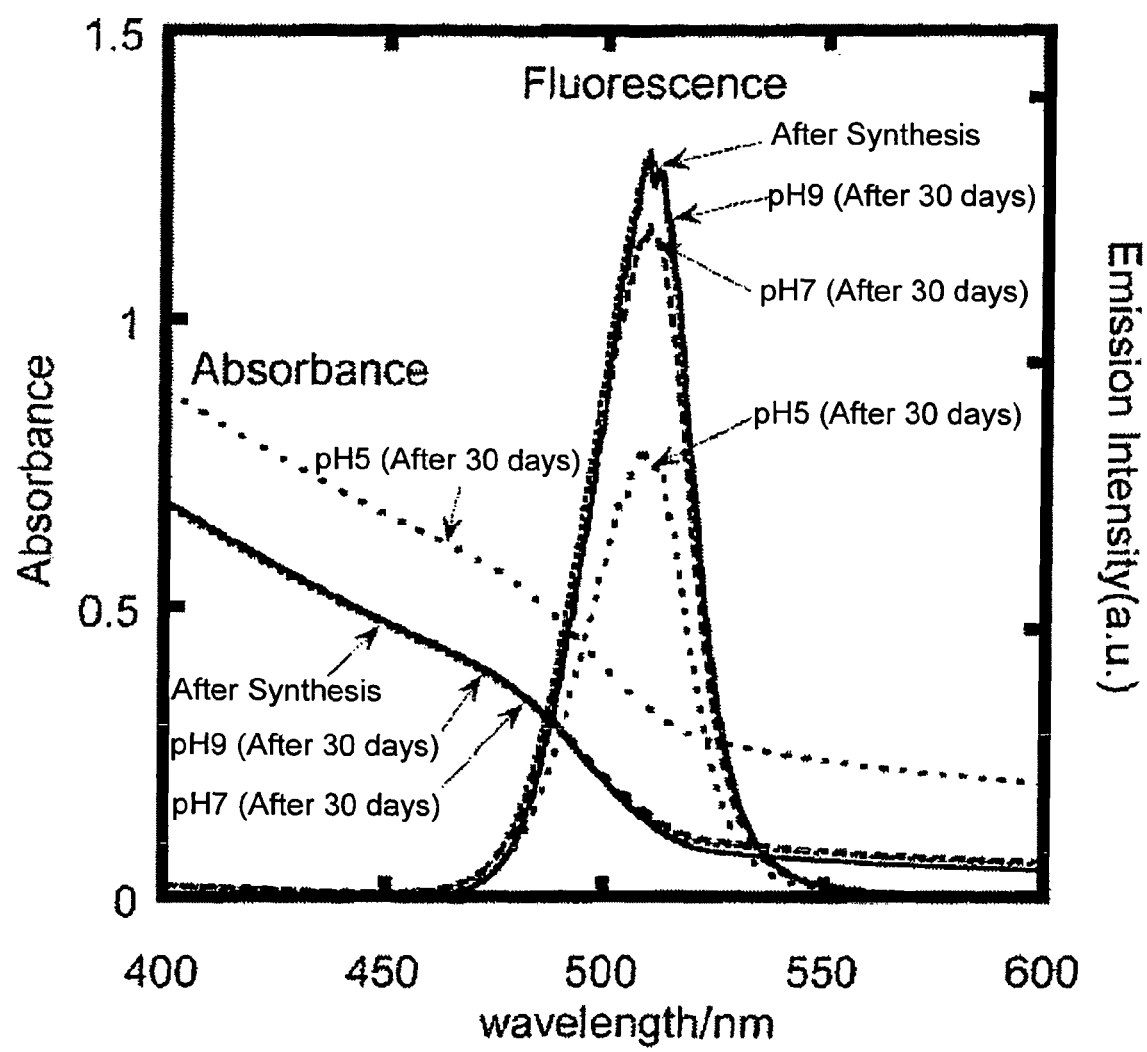
FIG. 7 shows absorbance and fluorescence spectra together with durability of a semiconductor nanoparticle synthesized according to the example 2.

Polyacrylic acid (average molecular weight: 5000) and ethylenediamine were added to the obtained optically clear yellow solution to concentrations of 0.1 mM and 1.5 mM therein, respectively, followed by agitation for some time. Further, hydrochloric acid 1-ethyl-3-(3-dimethylaminopropyl)carbodiimide was added thereto to a concentration of 10 mM therein, followed by agitation for several days. Thereafter, the resultant was ultra-filtered so as to be refined. A schematic drawing, fluorescence spectra, and transmission electron microscope (TEM) pictures from such time are shown in FIGS. 4, 5, and 6, respectively.

Particle having further improved durability can be synthesized by arbitrarily selecting the types of surfactants and crosslinking agents for use, the types of solvents and methods for replacing the solvents, temperature conditions, etc.

Example 2

CdS nanoparticles perfectly dispersed into the organic solvent obtained as mentioned above (10 ml) were put into an eggplant shaped flask, and then hexane was removed by evaporation. 2 ml of chloroform was added and octadecylamine was added thereto to a concentration of 0.5 mM, and then, they were dissolved using ultrasonic wave. Further, the chloroform was removed by evaporation, and 2 ml of THF was added thereto for dissolving the nanoparticles again. Here, ultrasonic treatment may be used. Then, 10 ml of ultrapure water and a stirring bar were put into an eggplant shaped flask, and CdS nanoparticles dissolved in THF were rapidly poured thereto while agitated by the stirrer. The solution was dissolved by ultrasonic treatment, etc, only THF was removed by evaporation for obtaining a water solution, and then, the water solution was put into a centrifuge tube for removing precipitation by centrifugation. Thereby, water-soluble nanoparticles with amino groups arranged on the surfaces thereof were obtained.

10 ml of the obtained solution and a stirring bar were put into an eggplant shaped flask, and 50 μl of 0.2 M-polyacrylic acid adjusted to pH 7 was added thereto, and agitated by the stirrer for one hour. 1 μl of ethylenediamine is added thereto and agitated by the stirrer for ten minutes, and then, 19.2 mg of WSC was added and further agitated by the stirrer overnight. In this case, the polyacrilic acids binding to the surfaces of the particles are crosslinked by ethylenediamine. When amine is used as amphipathic molecules to make the nanoparticles water-soluble, this amine also binds to the polyacrilic acids. This solution was put into the centrifuge tube for removing precipitation by centrifugation, and then, flow cleaning was carried out using ultrafiltration equipment of 50 ml cells. Although precipitation was produced under an acidic region, the obtained particles continued to maintain the same fluorescence property for more than one month under regions of pH 5 to 9 in pure water.

Each of the nanoparticles obtained according to either the example 1 or 2 has a carboxyl group exposed on the surface thereof. Such configuration is preferable for staining and labeling of biopolymers.

As described above, the present invention is not especially limited with respect to the material of particles, the types of surfactants and crosslinking agents for use, the types of polymers to be electrostatically bound, the types of solvents and methods for replacing the solvents, concentration and temperature conditions, etc. Further, characteristic improvements in dispersibility and durability can be realized by arbitrarily selecting these conditions, and the surface design of varying the types of functional groups to be exposed to the surface or the like can be flexibly performed. Furthermore, with the use of the method of the present invention, semiconductor particles having an entirely positively charged surface condition and those having a negatively charged surface condition can alternately be laminated on each other, so that the improvement of durability of the particles can be attempted. In addition, crosslinking using ethylenediamine was carried out in the Examples, while polymers used may contain a portion capable of being crosslinked. Further, in the present invention, particle size control is not particularly carried out. It is also possible to obtain fine particle sizes using an ultrasonic homogenizer, etc.; however, any particle size can be appropriate.

According to the present invention, it becomes possible to easily synthesize semiconductor nanoparticles that have high luminescence properties and excellent chemical stability. The semiconductor nanoparticles of the present invention can be used for fluorescent reagents and optical devices, etc. by utilizing such high luminescence properties.

What is claimed is:

1. A modified semiconductor nanoparticle, which is modified with a functional group-containing polymer which is electrostatically bound to a semiconductor nanoparticle to form a modified semiconductor.

2. The modified semiconductor nanoparticle according to claim 1, wherein electron-releasing groups are arranged on the surface of said semiconductor nanoparticle and said polymer is electrostatically bound to the outside of said electron-releasing groups.

3. The modified semiconductor nanoparticle according to claim 1, wherein said functional group-containing polymer forms a crosslinking bond via a crosslinking agent.

4. The modified semiconductor nanoparticle according to claim 1, wherein said functional group-containing polymer is bound to the surface of the semiconductor nanoparticle via a semiconductor nanoparticle-coating compound.

5. The modified semiconductor nanoparticle according to claim 1, comprising said functional group-containing polymer whose functional group is one or more functional groups selected from the group consisting of —COOH, —OH, —NH$_2$, —SH, —OCN, —CNO, —CHO, —CH=O, —CH=CH$_2$, and —C≡CH.

6. The modified semiconductor nanoparticle according to claim 3, wherein said crosslinking bond is one or more bonds selected from the group consisting of an ester bond, an amide bond, an imide bond, an ether bond, a urethane bond, a sulfide bond, a polysulfide bond, a carbonate bond, a thiol bond, a thioester bond, and a thiourethane bond.

7. The modified semiconductor nanoparticle according to claim 3, wherein said crosslinking bond results from carbon-carbon double bond or carbon-carbon triple bond polymerization.

8. The modified semiconductor nanoparticle according to claim 3, wherein said functional group-containing polymer is polyacrylic acid and said crosslinking agent is alkylene diamine.

9. The modified semiconductor nanoparticle according to claim 2, wherein said electron-releasing group is at least one electron-releasing group selected from the group consisting of —OR, —OCH$_2$R, —OCOCH$_2$R, —NHR, —N(CH$_2$R)$_2$, —NHCOCH$_2$R, —CH$_2$R, and —C$_6$H$_4$R, where R is hydrogen, a substituted hydrocarbon group, or an unsubstituted hydrocarbon group.

10. The modified semiconductor nanoparticle according to claim 4, wherein said semiconductor nanoparticle surface-coating compound is one or more compounds selected from the group consisting of primary amines (R$_1$NH$_2$), secondary amines (R$_1$R$_2$NH), tertiary amines (R$_1$R$_2$R$_3$N), and quaternary ammonium compounds (R$_4$R$_5$R$_6$R$_7$N$^+$), where R$_1$ to R$_7$ are each hydrogen, a substituted hydrocarbon group, or an unsubstituted hydrocarbon group.

11. The modified semiconductor nanoparticle according to claim 10, wherein R$_1$ to R$_7$ comprise a substituent at a terminal opposite to an amino group or ammonium group.

12. The modified semiconductor nanoparticle according to claim 1, comprising a semiconductor nanoparticle whose material is one or more materials selected from the group consisting of ZnO, ZnS, ZnSe, ZnTe, CdO, CdS, CdMnS, CdSe, CdMnSe, CdTe, CdMnTe, HgS, HgSe, HgTe, InP, InAs, InSb, InN, GaN, GaP, GaAs, GaSb, TiO$_2$, WO$_3$, PbS, PbSe, MgTe, AlAs, AlP, AlSb, AlS, Ge, and Si, or a semiconductor nanoparticle having a multilayer structure consisting of a core portion and a shell portion that are made of one or more members of said group.

13. The modified semiconductor nanoparticle according to claim 1, wherein the particle size of said semiconductor nanoparticle exhibits a deviation of less than 10% rms in diameter, thereby achieving monodispersion.

14. The modified semiconductor nanoparticle according to claim 1, wherein said semiconductor nanoparticle emits light in a narrow spectrum range of less than 60 nm in terms of full width at half maximum (FWHM) upon being irradiated with excitation light.

15. A fluorescent reagent comprising a modified semiconductor nanoparticle, which is modified with a functional group-containing polymer which is electrostatically bound to a semiconductor nanoparticle to form a modified semiconductor.

16. An optical device comprising a modified semiconductor nanoparticle, which is modified with a functional group-containing polymer which is electrostatically bound to a semiconductor nanoparticle to form a modified semiconductor.

* * * * *